(12) United States Patent
Gilbertson

(10) Patent No.: US 6,665,058 B1
(45) Date of Patent: Dec. 16, 2003

(54) DEVICE FOR JUDGING SYMMETRY, BRIGHTNESS, AND EFFICIENCY OF LIGHT RETURN IN PRECIOUS STONES

(75) Inventor: Al Gilbertson, Albany, OR (US)

(73) Assignee: EightStar Diamond Company, Inc., Cotati, CA (US)

( * ) Notice: Subject to any disclaimer, the term of this patent is extended or adjusted under 35 U.S.C. 154(b) by 0 days.

(21) Appl. No.: 09/578,058

(22) Filed: May 24, 2000

(51) Int. Cl.[7] ................................................ G01N 21/00
(52) U.S. Cl. ...................................................... 356/30
(58) Field of Search ........................ 356/30, 31, 416, 356/419

(56) References Cited

U.S. PATENT DOCUMENTS

| | | | |
|---|---|---|---|
| 4,647,194 A | | 3/1987 | Shigetomi et al. |
| 5,196,966 A | | 3/1993 | Yamashita |
| 5,260,763 A | | 11/1993 | Yamashita |
| 5,430,538 A | * | 7/1995 | Kobayashi .................... 356/30 |
| 6,348,964 B1 | * | 2/2002 | Wagner et al. ................. 356/30 |

* cited by examiner

Primary Examiner—Frank G. Font
Assistant Examiner—Layla Lauchman
(74) Attorney, Agent, or Firm—Miller Nash LLP

(57) ABSTRACT

The invention is a multicolored reflecting disc that can be mounted to a lens for grading gemstone brightness and symmetry. The disc has an opening or aperture through which the gemstone is viewed on the object side of the lens. The aperture is surrounded by multicolored concentric rings which face the gemstone. Light reflecting from the multicolored rings creates specific colors on the gemstone that allow symmetry and brightness of the tone to be evaluated.

2 Claims, 6 Drawing Sheets

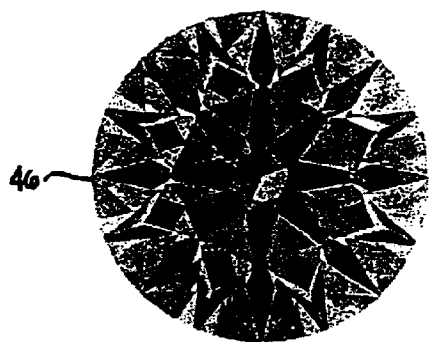
FIG. 5
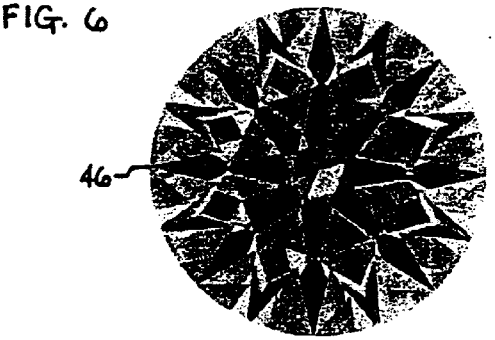
FIG. 6
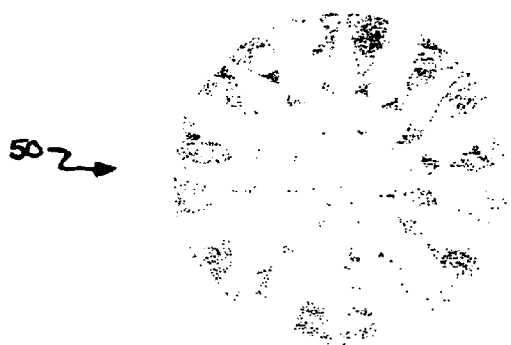

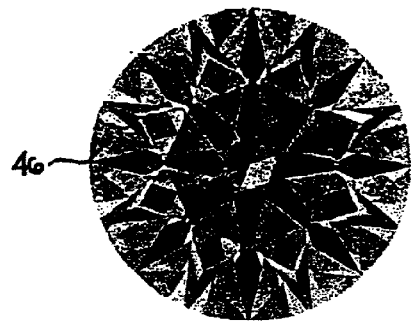
FIG. 7
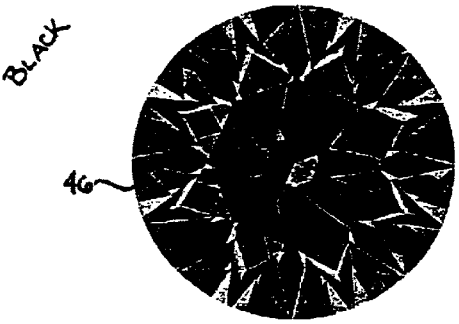
FIG. 8
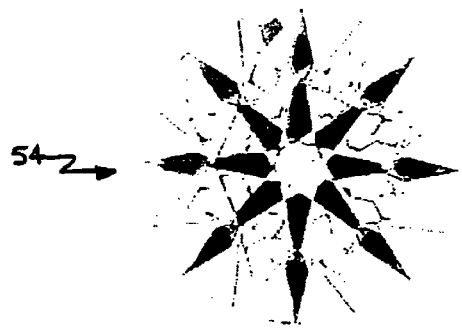

DEVICE FOR JUDGING SYMMETRY, BRIGHTNESS, AND EFFICIENCY OF LIGHT RETURN IN PRECIOUS STONES

TECHNICAL FIELD OF THE INVENTION

The present invention relates to a device for observing and analyzing the quality of precious stones, especially diamonds, and in particular to a device which provides relevant information regarding a stone's symmetry, brightness, and efficiency of light return.

BACKGROUND OF THE INVENTION

While a significant part of a diamond's value is determined by its weight or carat, the popularity of diamonds as gem stones is due in large part to their inestimable brilliance. The degree of a diamond's brilliance is influenced significantly by its cut, transparency, clarity, and color.

When diamonds are cut to traditional "ideal" cut angles and the facets are carefully aligned to facilitate "mirroring," light leakage can be minimized and a greater percentage of light will be returned to the viewer, thereby giving the diamond a brighter appearance. "Mirroring" refers to the reflection of light to form symmetrical geometric patterns, wherein the facets work together to collect light and return the maximum amount of light to the viewer.

Brightness, however, is a function of several attributes of cutting. Even though light may not be "leaking" or passing through the rear side ("pavilion") of the diamond, there is no guarantee that large amounts of light are being returned to the viewer. In order to evaluate the efficiency of light return, light must be gathered from around the viewer, and its reflective pattern analyzed.

Heretofore invented has been a device (see U.S. Pat. No. 4,647,194) which relates to the judging of brilliancy in diamonds by viewing a stone through a magnifying lens wherein the object side of the lens is fitted with a solid red colored disc having a centrally-located hole. Viewing the diamond through the lens assembly provides the viewer with an image of the diamond in which those areas which are reflecting light to the viewer appear as red, whereas those areas of the diamond not reflecting light, but leaking light through the pavilion, appear colorless. This observation allows the viewer to form a general conclusion about the light reflective properties or brilliancy of the particular stone.

The prior art device does not, however, permit the angles of reflective light to be analyzed. Consequently, no information is available regarding the stone's symmetry or the efficiency of light return based on the cut of the diamond. Without such information, faults in the diamond's cut may not be apparent, particularly to an inexperienced purchaser. Such faults may significantly impact the appearance of the gem stone and detract from its total value.

SUMMARY OF THE INVENTION

It is an object of the present invention to address the aforementioned problem and provide a device with which a viewer may judge a stone's brightness and symmetry via the observed efficiency of light return from various angles of incidence upon the diamond.

The device of the present invention comprises a simple body wherein a precious stone such as a diamond is placed between a light source and a magnifying lens. The lens is equipped, on the object side, with a multicolored disc wherein each color represents a ring around a portion of the disc, and wherein the stone is viewed through a centrally-located hole in said disc.

Light from the light source is reflected from each colored ring onto the diamond's surface at an angle defined by the ring's position from the center of the disc through which the observer views the diamond. Because each angle or range of angles is represented by a specific color, light return efficiency can be analyzed and the symmetry and brightness of the stone evaluated.

Other objects, advantages, and features of the present invention will be apparent to the reader from the foregoing and the appended claims, and as the ensuing detailed description and discussion of the invention proceeds in conjunction with the accompanying drawings.

BRIEF DESCRIPTION OF THE DRAWINGS

In the drawings, like reference numerals refer to like parts throughout the various views unless indicated otherwise, and wherein:

FIG. 5 illustrates the image of an observed diamond with the red portion of the image shown separately;

FIG. 6, like FIG. 5, illustrates the image of an observed diamond with the green portion of the image shown separately;

FIG. 7, like FIGS. 5 and 6, illustrates the image of an observed diamond with the dark blue portion of the image shown separately;

FIG. 8, like FIGS. 5–7, illustrates the image of an observed diamond with the black portion of the image shown separately;

DETAILED DESCRIPTION OF THE INVENTION

Figure 1:
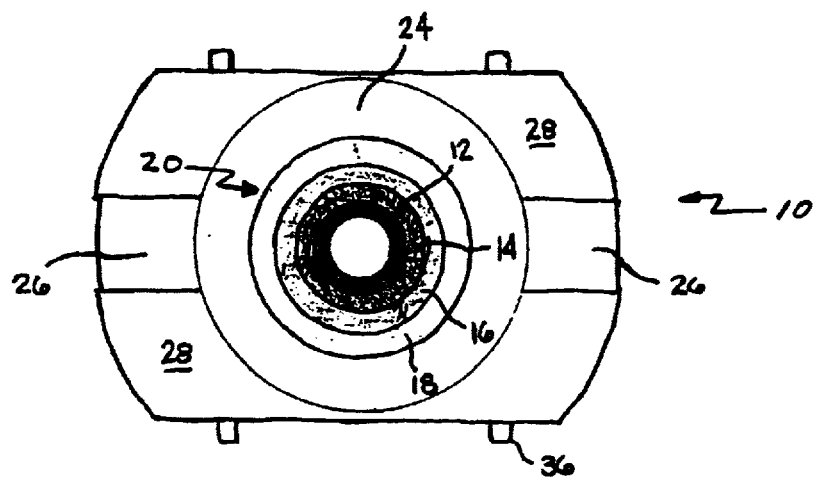
FIG. 1 is a bottom plan view of a lens bracket embodying the principles of the present invention.
Figure 1A:
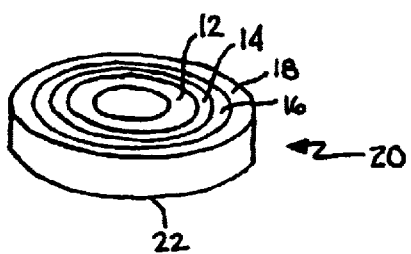
FIG. 1A is a perspective view of a multicolored reflecting disc.

Referring now to the drawings, FIG. 1 illustrates the underside of a lens bracket generally at 10. Colored rings 12, 14, 16, and 18 are fixedly secured to the surface of a disc 20 (see FIG. 1A) via an adhesive or other appropriate method. Disc 20 is a cylinder, open at one end 22, and capable of being fitted and frictionally secured to the object side of a magnifying lens 30 (see FIGS. 3, 4).

The colors respectively associated with each ring of the disc 20 are irrelevant, but should be chosen to easily permit the observer to distinguish between the various colors since each color represents a distinct range of angles from which light is incident upon the top surface ("table") of the diamond. In the present embodiment used for illustrative purposes herein, each ring is associated with the following color: Ring 12 is red; ring 14 is green; ring 16 is dark blue;

and ring 18 is light blue. Circular recess 24 and longitudinally extending slot 26 of lens bracket 10 are also colored similarly to the outermost ring 18, in this case light blue. The remaining portion 28 of the underside of lens bracket 10 is outside the critical angle and is not reflected to the overhead viewer by the diamond. This portion of the lens bracket is black in color. It should be noted that the overhead viewer may in fact observe a black reflection from the diamond as illustrated in FIG. 8. This black portion of the image is formed by reflected light that entered the diamond from 90 to 75 degrees to the table and generally represents the image of the overhead viewer as he or she observes the diamond through magnifying lens 30.

Figure 2:
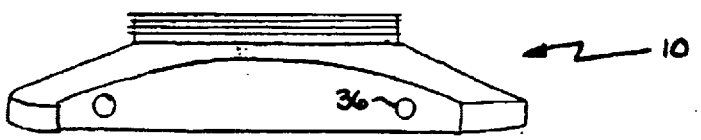
FIG. 2 is a side elevational view of the lens bracket illustrated in FIG. 1.
Figure 3:
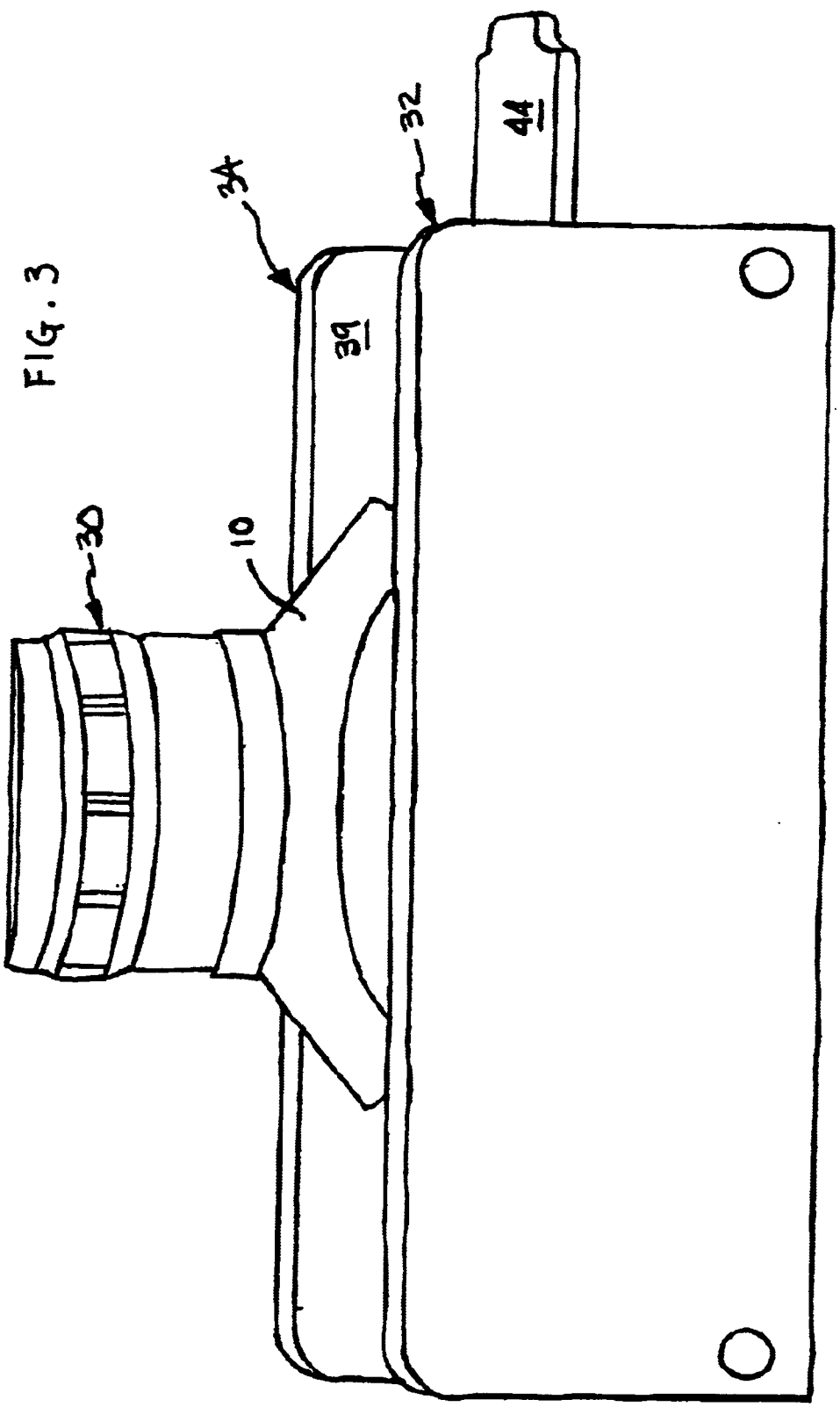
FIG. 3 is a front perspective view of a viewing device which may incorporate the principles of the present invention.
Figure 4:
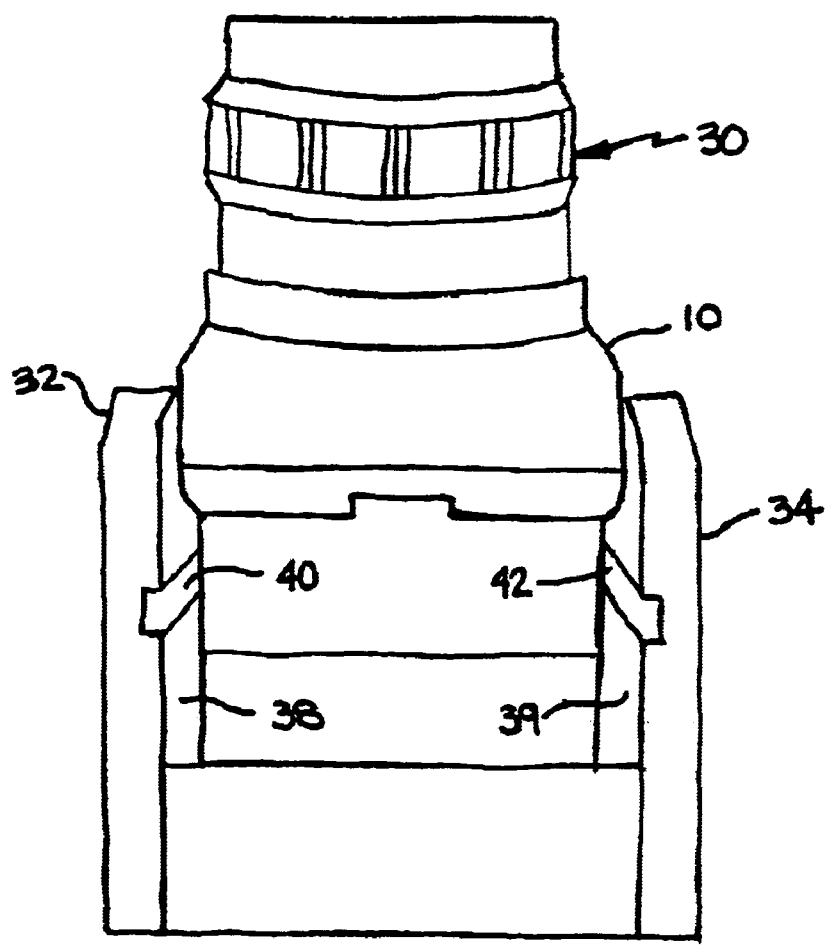
FIG. 4 is a side perspective view of the device illustrated in FIG. 3.

Referring now primarily to FIGS. 2–4, lens bracket 10 is mounted between a first grooved side wall 32 and a second grooved side wall 34. Lens bracket 10 is secured between first and second grooved side walls 32, 34 by extending pins 36 which are received in spaced openings (not shown) machined into the inner surfaces 38, 39 of grooved side walls 32, 34. Grooves 40, 42 extend longitudinally along the inner surfaces 38,39 of grooved side walls 32,34 to receive sliding plate 44.

A row of conical depressions (not shown) machined into the surface of sliding plate 44 support diamonds of various sizes and permit the user to position a particular stone directly below magnifying lens 30 for observation. After the selected diamond has been positioned below magnifying lens 30, the user activates the light source located below the diamond and sliding plate 44, and can then evaluate the symmetry, brightness, and sufficiency of light return for the particular stone.

Turning now to FIGS. 5–8, the image of a substantially symmetrical diamond 46 is illustrated in association with the separate image of a portion of the light reflected to the overhead viewer. The multicolored image of the substantially symmetrical diamond 46 is a composite of light incident upon the crown of the diamond from all angles greater than the critical angle. This image is that which is observed by the overhead viewer. In correspondence with the illustrative selected colors set forth above, FIG. 5 illustrates the red portion of the image 48 which is that light that is incident upon the crown of the diamond from 75 to 65 degrees and then reflected directly to the overhead viewer. FIG. 6 illustrates the green portion of the image 50 which is that light that is incident upon the crown of the diamond from 65 to 55 degrees and then reflected directly to the overhead viewer. FIG. 7 illustrates the dark blue portion of the image 52 which is that light that is incident upon the crown of the diamond from 55 to 45 degrees and then reflected directly to the overhead viewer. FIG. 8 illustrates the black portion of the image 54 which is that light that is incident upon the crown of the diamond from 90 to 75 degrees and then reflected directly to the overhead viewer. The remainder of the composite image 46 consists of light blue portions representing light incident upon the crown of the diamond at less than 45 degrees, but greater than the critical angle.

Figure 9:
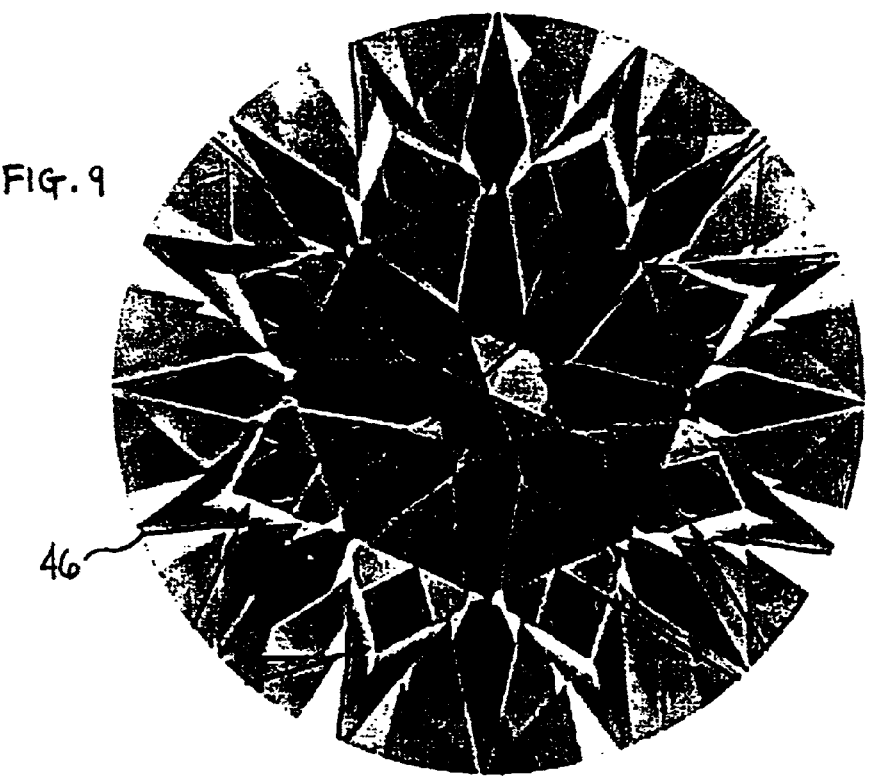
FIG. 9 illustrates the image of an observed diamond that is substantially symmetrical.
Figure 10:
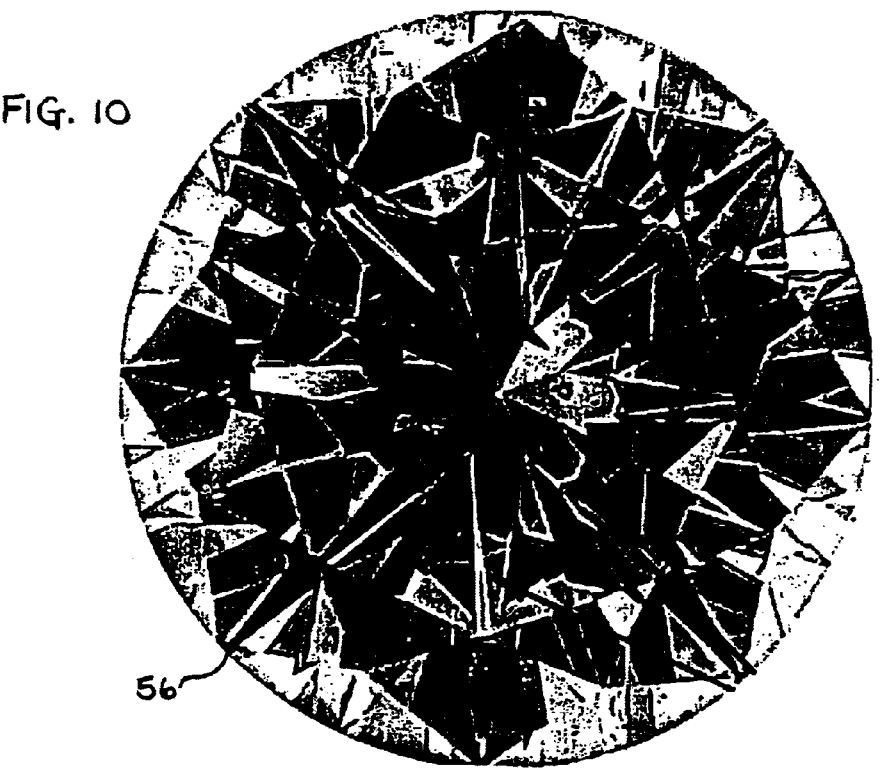
FIG. 10 illustrates the image of an observed diamond that is less symmetrical than the diamond illustrated in FIG. 9.

FIG. 9 is a larger image of the multicolored composite image illustrated at 46 in FIGS. 5–8 demonstrating the symmetrical nature of the particular gemstone viewed through magnifying lens 30. FIG. 10 illustrates the multicolored composite image 56 of a less symmetrical diamond as viewed under the same conditions through the magnifying lens. The erratic table reflections shown in this image illustrate the lack of symmetry in this particular gemstone. Such erratic reflections limit the brilliance of the stone and may detract from its overall value.

The multicolored rings 12, 14, 16, and 18 define at least two differently colored areas on the disc surface 20 facing away from the lens 30 and toward the gemstone. While it is believed that the concentric, multicolor ring arrangement described above is preferred, it may be possible to accomplish the same function by simply using different colored surface areas that have another geometric arrangement. Therefore, while the invention is described and illustrated here in the context of diamonds, and with particular color selections for the rings of the multicolored disc, the invention may be embodied in many forms without departing from the spirit or essential characteristics of the invention. The present embodiment is therefore to be considered in all respects as illustrative and not restrictive. The scope of the invention is indicated by the appended claims rather than by the foregoing description, and all changes which come within the meaning and range of equivalency of the claims are intended to be embraced therein.

What is claimed is:

1. An invention that is used in conjunction with a lens for judging a gemstone's brightness and symmetry comprising:

a surface that is directly attached to the lens facing away from the lens;

an aperture through the surface for allowing the gemstone to be viewed on the object side of the lens, and a plurality of concentric rings arranged on the surface, at least one ring having a different color from another.

2. An invention that is used in conjunction with a lens for judging a gemstone's brightness and symmetry, comprising:

a surface that is directly attached to the object side of the lens facing away from the lens, an aperture through the surface for allowing the gemstone to be viewed on the object side of the lens, and a plurality of colored areas on the surface, at least one of such areas having a different color from another.

* * * * *